United States Patent [19]

Yoshioka et al.

[11] 4,347,316
[45] Aug. 31, 1982

[54] PROCESS FOR ISOMERIZING GLUCOSE TO FRUCTOSE

[75] Inventors: Toshio Yoshioka; Kazuo Teramoto; Masaharu Shimamura, all of Ohtsu, Japan

[73] Assignee: Toray Industries, Inc., Tokyo, Japan

[21] Appl. No.: 266,155

[22] Filed: May 22, 1981

Related U.S. Application Data

[63] Continuation of Ser. No. 114,270, Jan. 22, 1980, Pat. No. 4,275,156.

[30] Foreign Application Priority Data

Jan. 23, 1979 [JP] Japan .................................. 54/6727

[51] Int. Cl.³ ............................................ C12P 19/24
[52] U.S. Cl. ...................................................... 435/94
[58] Field of Search ......................................... 435/94

[56] References Cited

U.S. PATENT DOCUMENTS

| | | | |
|---|---|---|---|
| 3,708,397 | 1/1973 | Sipos ........................ | 435/94 |
| 3,788,945 | 1/1974 | Thompson et al. .......... | 435/94 |
| 4,078,970 | 3/1978 | Fujita et al. ................ | 435/180 |

*Primary Examiner*—Lionel M. Shapiro
*Attorney, Agent, or Firm*—Austin R. Miller

[57] ABSTRACT

An enzymatically active product for use in isomerization of glucose into fructose is provided. The active product comprises an organic polymeric material predominantly comprised of a monovinyl aromatic compound polymer having β-aminopropionamidomethyl group as side chains represented by the formula I:

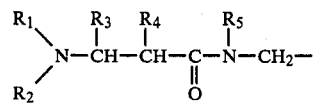

wherein $R_1$ is selected from H, C(1-6) alkyl and C(2-6) hydroxyalkyl, $R_2$ is selected from C(1-6) alkyl, C(2-6) hydroxyalkyl,

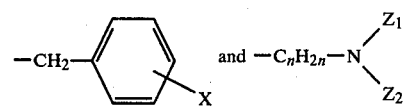

(where X, $Z_1$ and $Z_2$ are selected from H and C(1-6) alkyl, and n is from 2 to 6), or $R_1$ and $R_2$ form together with the N atom, to which $R_1$ and $R_2$ are bonded, heterocyclic structure of the formula:

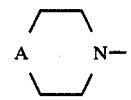

where A is —$CH_2$—, —O— or —$NR_6$— (wherein $R_6$ is H or C(1-6) alkyl), and $R_3$, $R_4$ and $R_5$ are selected from H and methyl. The organic polymeric material has glucose isomerase immobilized with the β-aminopropionamidomethyl group side chain of the organic polymeric material.

13 Claims, No Drawings

PROCESS FOR ISOMERIZING GLUCOSE TO FRUCTOSE

This is a continuation of application Ser. No. 114,270 filed Jan. 22, 1980, now U.S. Pat. No. 4,275,156, issued June 23, 1981.

BACKGROUND OF THE INVENTION (1) Field of the Invention

This invention relates to a process for isomerizing a glucose-containing solution to convert at least a part of the glucose to fructose.

(2) Description of the Prior Art

Glucose isomerase is an enzyme capable of converting glucose into fructose and vice versa and is used for producing fructose from glucose.

Many proposals have been made to stabilize and/or to immobilize glucose isomerase for the multiple reuse thereof. For example, U.S. Pat. Nos. 3,708,397 and 3,788,945 teach the immobilization of glucose isomerase with DEAE, TEAE or ECTEOLAcellulose. These celluloses are used in the form of a microgranule, fine fiber or a cake. These forms are not convenient to handle. Furthermore, when these celluloses are packed in a column, they tend to be densified during the use, and hence, cause a large pressure loss and prevent the passage of a glucose substrate solution. Japanese Laid-open Patent Application 53,582/1975 discloses the immobilization of glucose isomerase with a macroreticulated or porous anion exchange resin. However, the isomerase immobilized anion exchange resin exhibits an undesirably low enzymatic activity and is also poor in the retention of activity. Japanese Laid-open Patent Applications 1181/1973 and 92,277/1974 teach that a homogenized microorganism cell concentrate containing ruptured cells is treated with glutaraldehyde to form a crosslinked coherent solid product. This crosslinked product is also not satisfactory in its enzymatic activity. Furthermore, once the enzymatic activity of the crosslinked product decreases due to repeated use, it is difficult or even impossible to regenerate its enzymatic activity.

SUMMARY OF THE INVENTION

An object of the present invention is to provide a process for isomerizing a glucose-containing solution to convert at least a part of the glucose to fructose by a process of isomerization.

Another object of the present invention is to provide a process for producing an isomerized glucose-containing solution, containing fructose, which is suitable for subsequent separation.

Still another object of the present invention is to provide such a process which enhances fructose productivity.

Other objects and advantages of the present invention will be apparent from the following description.

The enzymatically active product which is useful in the process of the invention for use in isomerization of glucose into fructose comprises an organic polymeric material comprised of at least 50% by weight, based on the weight of the organic polymeric material, of a monovinyl aromatic compound in polymerized form. The polymerized monovinyl aromatic compund has a β-aminopropionamidomethyl group as a side chain represented by the formula I:

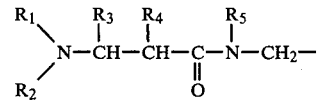

wherein $R_1$ is selected from hydrogen, an alkyl group having 1 to 6 carbon atoms and a hydroxyalkyl group having 2 to 6 carbon atoms; $R_2$ is selected from an alkyl group having 1 to 6 carbon atoms, a hydroxyalkyl group having 2 to 6 carbon atoms;

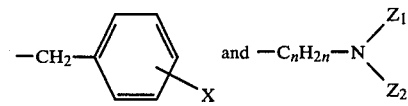

(where X, $Z_1$ and $Z_2$ are selected from hydrogen and an alkyl group having 1 to 6 carbon atoms, and n is an integer of from 2 to 6); or $R_1$ and $R_2$ form together with the nitrogen atom, to which $R_1$ and $R_2$ are bonded, a heterocyclic structure represented by the formula

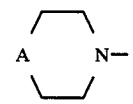

where A is $-CH_2-$, $-O-$ or $-NR_6-$ ($R_6$ is H or an alkyl group having 1 to 6 carbon atoms); and $R_3$, $R_4$ and $R_5$ may be the same as or different from each other and are selected from hydrogen and a methyl group. The organic polymeric material has glucose isomerase immobilized with the β-aminopropionamidomethyl group side chain of the organic polymeric material.

The enzymatically active product of the invention is prepared by a process which comprises the steps of (a) treating an article of an organic polymeric material comprised of at least 50% by weight, based on the weight of the organic polymeric material, of a monovinyl aromatic compound in polymerized form, with an acrylamidomethylating agent represented by the formula II:

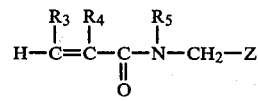

wherein $R_3$, $R_4$ and $R_5$ are as defined above with respect to the formula I, and Z is

where $R_6$ is selected from hydrogen, an alkyl group having 1 to 6 carbon atoms and

($R_7$ is an alkyl group having 1 to 6 carbon atoms), or

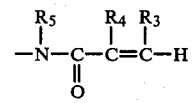

where $R_3$, $R_4$ and $R_5$ are as defined above; (b) treating the article with an amino compound represented by the formula III:

wherein $R_1$ and $R_2$ are as defined above with respect to the formula I, thereby introducing to the polymerized monovinyl aromatic compound a $\beta$-aminopropionamidomethyl group as a side chain represented by the above-mentioned formula I, and; then, (c) bringing the article into contact with a glucose isomerase-containing solution or dispersion to immobilize glucose isomerase with said side chain of the polymerized monovinyl aromatic compound.

DESCRIPTION OF THE PREFERRED EMBODIMENTS

The organic polymeric material, with which glucose isomerase is to be immobilized, in the practice of the process of this invention, may be a homopolymer of a monovinyl aromatic compound or a copolymer (including a graft copolymer) comprised of at least 50% by weight of units derived from a monovinyl aromatic compound and not more than 50% by weight of at least one other copolymerizable monomers. The monovinyl aromatic compound used includes, for example, styrene, $\alpha$-methystyrene, vinyltoluene, vinylxylene and chlorostylene. The copolymerizable monomers used include, for example, methyl acrylate, methyl methacrylate, acrylonitrile, acrylamide, vinyl chloride and vinylidene chloride.

The above-mentioned organic polymeric material predominantly comprised of the monovinyl aromatic compound in polymerized form (which material is hereinafter referred to as "monovinyl aromatic compound polymer" for brevity) may be employed in combination with other polymeric materials. The polymeric materials used are those which are miscible but substantially incompatible with the monovinyl aromatic compound polymer. Such polymeric materials include, for example, polyolefins, polyamides, polyesters and their copolymers. The organic polymeric material predominantly comprised of the monovinyl aromatic compound and the other polymeric material may be used either as a blend or so that these polymeric materials form discrete portions of the article with which glucose isommerase is immobilized. The proportion of the monovinyl aromatic compound polymer to the other polymeric material is not particularly limited, provided that the monovinyl aromatic compound polymer is exposed to the surface of the article, with which the isomerase is immobilized, to an extent such that the monovinyl aromatic compound polymer occupies at least about one half of the entire surface area of the article.

The shape of the article, with which glucose isomerase is immobilized, is not particularly limited, but the article may usually be in the form of a fiber, a particulate or a film. One preferable form of the article is a fiber comprised of the monovinyl aromatic compound polymer and another fiber-forming organic polymeric material. The fiber may be either a blend fiber made from a uniform blend of the two polymeric materials, or a core-sheath type or islands-in-a-sea type composite fiber, the sheath or sea ingredient being predominantly comprised of the monovinyl aromatic compound polymer and the core or island ingredient being comprised of the fiber-forming organic polymeric material. Of these fibers, the blend fiber and the islands-in-a-sea type composite fiber are most preferable because of their good resistance to separation. It is particularly preferable that the number of islands in a sea in the cross-section of the islands-in-a-sea type composite fiber be at least 5.

In the blend fiber, the amount of the fiber-forming organic polymeric material should preferably be less than 50% by weight, based on the total weight of the fiber-forming organic polymeric material and the monovinyl aromatic compound polymer. When the amount of the fiber-forming organic polymeric material exceeds 50% by weight, the enzymatically active product resulting from the blend fiber cannot immobilize the desired amount of glucose isomerase. There is no particularly critical lower limit for the amount of the fiber-forming organic polymeric material, but it is preferable to use from 20% to 40% by weight of the fiber-forming organic polymeric material for improving the mechanical strength of the fiber and the durability thereof.

In the core-sheath type or islands-in-a-sea type composite type, the amount of the sheath or sea ingredient predominantly comprised of the monovinyl aromatic compound polymer should preferably be in the range of from about 10 to 90% by weight, more preferably from about 20 to 80%, based on the weight of the composite fiber. When the amount of the core or island ingredient is less than about 10% by weight, the composite fiber becomes poor in mechanical strengths. In contrast, when the amount of the core or island ingredient exceeds about 90% by weight, the enzymatically active product resulting from the composite fiber becomes poor in the capacity of immobilizing glucose isomerase. The sheath or sea ingredient of the composite fiber may be a mixture of the monovinyl aromatic compound polymer and the fiber-forming organic polymeric material. In general, when the relative proportion of the fiber-forming organic polymeric material is large, the composite fiber becomes densified and, therefore, exhibits enhanced durability, mechanical strengths and resistance to separation, but the enzymatically active product resulting therefrom is poor in the capacity of immobilizing glucose isomerase. Thus, the amount of the fiber-forming organic polymeric material should preferably be less than about 50% by weight, more preferably in the range of from 5 to 40% by weight, based on the weight of the sheath or sea ingredient.

Both the blend fiber and the composite fiber may have either a circular cross-section or a non-circular cross-section. The fiber having a non-circular cross-section advantageously has a larger surface area than that of the circular sectional fiber. The blend fiber and the composite fiber may be of a porous structure, which has a far larger surface area than that of a non-porous structure.

The fineness of the blend fiber and the composite fiber is usually in the range of from about 0.01 to 500 deniers, preferably from about 0.1 to 50 deniers. When the fineness of the fiber is too small, the fiber possesses poor mechanical strengths and is liable to be broken into fine particles, and thus, is difficult to handle. In contrast, when the fineness of the fiber is too large, the enzymatically active product resulting from the fiber becomes poor in the capacity of immobilizing glucose isomerase.

The blend fiber and the composite fiber may be used in various forms, such as, for example, filament yarns, staple fibers, a needle-punched felt and other non-woven fabrics, woven fabrics, knitted fabrics and battings.

The monovinyl aromatic compound polymer has as a side chain the β-aminopropionamidomethyl group of the formula I, hereinbefore mentioned. The amount of the β-aminopropionamidomethyl group is preferably at least about 0.5 meq. more preferably in the range of from about 2.0 to 5.0 meq, per g of the monovinyl aromatic compound polymer. When the amount of the β-aminopropionamidomethyl group is less than about 0.5 meq/g, the monovinyl aromatic compound polymer is incapable of immobilizing the desired amount of glucose isomerase. Although there is no particularly critical upper limit for the amount of the β-aminopropionamidomethyl group, it is generally difficult to introduce more than about 5.0 meq/g, of the β-aminopropionamidomethyl group into the monovinyl aromatic compound polymer.

The enzymatically active product of the invention is prepared by the following process. In the first step, an article comprised of either the monovinyl aromatic compound polymer or a combination of the monovinyl aromatic compound polymer and the other polymeric material is treated with an acrylamidomethylating agent of the formula II, hereinbefore mentioned, whereby acrylamidomethyl groups are introduced as side chains to the monovinyl aromatic compound polymer.

As hereinbefore mentioned, the shape of the article to be treated with the acrylamidomethylating agent is not particularly limited, but the article is preferably in the form of a fiber comprised of the monovinyl aromatic compound polymer and another fiber-forming organic polymeric material. The fiber may be either a blend fiber, or a core-sheath type or islands-in-a-sea type composite fiber, the sheath or sea ingredient being predominantly comprised of the monovinyl aromatic compound polymer and the core or island ingredient being comprised of the fiber-forming organic polymeric material. The blend fiber and the composite fiber may be prepared by a conventional procedure. The monovinyl aromatic compound polymer used for the preparation of the blend or composite fiber preferably possess an intrinsic viscosity of from 0.5 to 5, as measured in toluene, at 25° C. Both the blend fiber and the composite fiber may be used in various forms as hereinbefore mentioned.

The treatment of the above-mentioned article with the acrylamidomethylating agent is usually effected in the presence of a swelling agent capable of swelling the monovinyl aromatic compound polymer and in the presence of an acid catalyst. The swelling agent used includes, for example, halogenated hydrocarbons, such as dichloromethane, carbon tetrachloride, dichloroethane, sym-tetrachloroethane and tetrachloroethylene, and; nitrated hydrocarbons, such as 1- or 2-nitropropane, nitroethane and nitrobenzene. These swelling agents may be used either alone or in combination. Of these swelling agents nitrated hydrocarbons are preferable.

The acid catalyst used includes, Friedel-Crafts catalysts such as, aluminum chloride, tin tetrachloride, ferric chloride and zinc chloride; strong organic acids, such as aliphatic sulfonic acids (e.g. methanesulfonic acid) and aromatic sulfonic acids (e.g. benzenesulfonic acid and toluenesulfonic acid), and; strong inorganic acids, such as sulfuric acid (particularly concentrated and fuming sulfuric acids). Of these acid catalysts, sulfuric acid is preferable.

The acrylamidomethylating agent represented by the formula II, hereinbefore mentioned, includes, for example, N-methylolacrylamide and its carboxylic acid esters and alkyl ether derivatives; N-methylolmethacrylamide and its carboxylic acid esters, and alkyl ether derivatives, and; N,N'-(oxydimethylen)bisacrylamide. These acrylamidomethylating agents may be used either alone or in combination. The amount of the acrylamidomethylating agent used should preferably be such that the resulting article contains from about 0.5 to 5.0 meq., more preferably from about 2.0 to 5.0 meq., per gram of the monovinyl aromatic compound polymer.

The acrylamidomethylating reaction may be preferably carried out at a temperature of from about 0° C. to about 60° C., more preferably from about 15° C. to about 30° C.

Prior to or during the acrylamidomethylating treatment, the article may be subjected to a crosslinking treatment wherein a crosslinking agent, such as formaldehyde, is used. The crosslinking treatment enhances the mechanical strengths of the article. It should be noted, however, that the crosslinking treatment reduces the capacity of the resulting product to immobilize glucose isomerase, and therefore, the degree of crosslinking should be to a minor extent.

The acrylamidomethylated product is then treated with an amino compound of the formula III, hereinbefore mentioned, whereby the acrylamidomethyl groups are converted to β-aminopropionamidomethyl groups. The amino compound used is not particularly limited, provided that the amino compound is capable of reacting with the acrylamidomethyl group, thereby converting the group to a β-aminopropionamidomethyl group. Preferable amino compounds are organoamino compounds (including multiamino compounds) having at least one primary or secondary amino group and forming little or no crosslinking. Such amino compounds include, for example, dimethylamine, diethylamine, dipropylamine, dibutylamine, dihexylamine, dipropanolamine, N-methylaminoethanol, N-methylbenzylamine, N,N-diethyl-N'-methylethylenediamine, methylamine, ethylamine, propylamine, butylamine, hexylamine, propanolamine, N,N-dimethylaminopropylamine, ethylenediamine, hexamethyldiamine, N,N-diethylethylenediamine, morpholine, piperidine and piperazine. These amino compounds may be used either alone or in combination.

The aminating treatment is usually effected in the presence of a solvent capable of dissolving the amino compound. The solvent used includes, for example, water; lower alcohols, such as methanol, ethanol and n-butanol, and; ethers, such as dioxane and tetrahydrofuran. The reaction temperature may be in the range of from room temperature to the reflux temperature. The reaction pressure may be normal. However, in the case where the amino compounds used has a low boiling point, the reaction pressure may be superatmospheric in order to shorten the reaction time.

The aminated product is then brought into contact with a glucose isomerase-containing solution or dispersion, whereby glucose isomerase is immobilized with the β-aminopropionamidomethyl group side chains of the aminated product.

Glucose isomerase can be obtained from various microorganisms which include, for example, actinomycetes, such as *Streptomyces phaseochromogenus* and *Streptomyces albus*, and; bacteria, such as *Bacillus coagulans*, *Bacillus megatherium*, *Lactobacillus brevis*, the Pseudomonas genus and the Aerobacter genus. Glucose isomerase may be used either in the form of a suspension containing ruptured cell pieces, extracted from microorganism cells, or in the form of a solution which is obtained by removing the ruptured cell pieces from the above-mentioned suspension by, for example, centrifuging or filtration, or which is obtained by refining the ruptured cell piece-removed solution.

The pH value of the glucose isomerase-containing solution or suspension may usually be in the range of from about 4 to 12. It is preferable, however, that the pH value be adjusted to the range of from about 5 to 9 in order to immobilize the desired large amount of glucose isomerase with the aminated product having β-aminopropionamidomethyl groups.

The procedure, by which the aminated product is brought into contact with the glucose isomerase-containing suspension or solution, is not particularly critical, but may be similar to that popularly employed in conventional ion exchange treatments. For example, the aminated product is immersed in the glucose isomerase-containing solution or dispersion, if desired while being stirred, and then, the product is washed with water. Alternatively, the glucose isomerase-containing solution or suspension is passed through a column packed with the aminated product in a fixed bed system, and then, the product is washed with water.

The β-aminopropionamidomethyl groups present in the aminated product may be either in the form of a salt, or a free form or a form bufferized with a suitable buffer. The aminated product having the free β-aminopropionamidomethyl groups preferably possesses a water content of from about 0.5 to 3. The water content usually varies depending upon the structure of the aminated product, the amount of the aminopropionamidomethyl groups present in the aminated product and the degree of crosslinking. When the water content is too small, it is difficult to immobilize the desired amount of the isomerase. In contrast, when the water content is too large, it becomes difficult to handle the aminated product.

The period of time and the temperature for the immobilizing treatment may suitably be determined so that the amount of glucose isomerase immobilized is as large as possible. In general, the amount of glucose isomerase immobilized may be varied in the range of from 2,000 to 50,000 U, particularly from 5,000 to 30,000 U, expressed in terms of the activity, per gram of the enzymatically active product.

In order to enhance the degree of activity retention of the resulting enzymatically active product, the isomerase-immobilized product may be treated with a solution containing a crosslinking agent, whereby the immobilized glucose isomerase is crosslinked with the crosslinking agent. Instead of treating the isomerase-immobilized product, the crosslinking agent may be incorporated in the glucose isomerase-containing solution used for immobilization. The crosslinking agent used is one which is capable of crosslinking a protein and is popularly called a multi-functional protein modifier. Such a crosslinking agent includes, for example, polyglutaraldehydes, such as glutaraldehyde dialdehyde starch, and; polyisocyanates, such as tolylene diisocyanate and hexamehtylene diisocyanate. When the degree of crosslinking is too large, the enzymatic activity of the product is liable to be low, although the degree of activity retention is high. Therefore, consideration should be given to the concentration of the crosslinking agent in the treating solution, the pH of the treating solution, and the treating temperature and time.

The enzymatically active product, particularly in the form of the blend fiber or the composite fiber, has the following advantages.

(i) The fibrous product has an enhanced activity per unit weight of the product.

(ii) The fibrous product exhibits a good retention of activity.

(iii) The fibrous product exhibits high mechanical strengths, good durability and good separation resistance.

(iv) The fibrous product can be used in an arbitrary form.

(v) The fibrous product has a low water content and is easy to handle.

(vi) The fibrous product can be produced by a simple procedure at a low production cost.

(vii) The fibrous product is capable of being regenerated when its enzymatic activity decreases after the repeated use thereof.

The regeneration of the product of the invention may be carried out as follows. The product is treated with an aqueous solution containing a water-soluble salt, mineral acid, alkali or their mixtures, and or an aqueous solution containing an oxidizing agent, such as hydrogen peroxide or sodium hypochlorite, whereby the deactivated isomerase is desorbed or decomposed. Then, the product is again brought into contact with the glucose isomerase-containing suspension or solution.

The isomerization of glucose into fructose may be carried out in either a continuous manner or a batchwise manner. The enzymatically active product may be incorporated in a glucose solution while being stirred, or a glucose solution may be passed through a column packed with the enzymatically active product in a fixed bed system.

The separation of fructose from the isomerized glucose solution may be carried out by a conventional procedure. It is, however, preferable to separate fructose from the isomerized glucose solution by the following procedure. That is, the isomerized glucose solution is brought into contact with zeolite having pores at least 5 angstroms in average diameter, whereby fructose and glucose contained in the isomerized glucose solution is adsorbed in the zeolite; and then, the adsorbed fructose is eluted from the zeolite particle.

The zeolite used for the separation of fructose may either by one naturally occurring or synthesized. The zeolite used is an aluminosilicate having a basket structure and represented by the formula: $(M_{2/n}O)_x \cdot (Al_2O_3)_y \cdot (SiO_2)_z \cdot (H_2O)_w$, where M is a cation, n is a valency of the cation, and x, y, z and w are mole numbers of the respective oxides and water. The zeolite has pores of relatively uniform pore diameters, and therefore, is popularly called a molecular sieve. The zeolite used includes, for example, X-type, Y-type and L-type faujasites (which are supplied by Union Carbide Corp. under the trade names Zeolite 13X, 10X, SK-40 and SK45) and moldenite (e.g. supplied by Norton Co. under the trade name Zeolon).

The zeolite used should preferably possess pores having an average diameter of at least 5 angstroms. When the average pore diameter is too small, the zeolite exhibits a poor capacity of adsorbing fructose.

The cation of the zeolite may preferably be, for example, univalent alkali metals, such as potassium, sodium, lithium and cesium, and bivalent alkaline earth metals, such as beryllium, magnesium, calcium, strontium and barium. Other metal ions, such as copper, silver, zinc, cadmium, aluminum, lead, iron and cobalt, and ammonium ions, such as $NH_4^+$ and $NH_3(CH_3)^+$, may also be used. These cations may be present in the zeolite either alone or in combination.

The ion exchange of the cation of the zeolite may be effected in a conventional manner. For example, sodium zeolite is incorporated in an aqueous 1 N solution of a nitrate of the metal to be exchanged. The mixture is maintained at a temperature of 60° C. for two hours, whereby the zeolite is infiltrated with the metal nitrate solution. This procedure is repeated several times. Then, the zeolite is completely washed with deionized water, dried at a temperature of 100° C. for 24 hours and, then, heat-treated at a temperature of about 400° C. for two hours.

The zeolite may be used in various forms, including finely divided particles and pellets. The pellets may be formed by using a binder for enhancing their mechanical strengths.

The adsorption of fructose and glucose contained in the isomerized glucose solution may be carried out in a conventional manner. The zeolite adsorbent may be used, for example, in a fixed bed system, a moving bed system or a fluidized bed system. The adsorption temperature may be normal, but an elevated temperature may also be employed for reducing the solution viscosity and enhancing the adsorption rate. However, when the adsorption temperature is too high, fructose and glucose are undesirably degraded. Therefore, the adsorption temperature should preferably be lower than about 100° C.

The desorption of the adsorbed fructose and glucose is carried out preferably by using a desorbent to which the zeolite exhibits an adsorptivity smaller than or equal to that to fructose and glucose, and which is capable of dissolving fructose and glucose. A preferable desorbent includes, for example, water and alcohols, such as methanol, ethanol and their mixtures.

The invention will now be further illustrated by the following examples in which parts are by weight unless otherwise specified.

In the examples, activity of glucose isomerase, water content, adsorption of albumin and activity efficiency were determined as follows.

(i) Activity of glucose isomerase

A glucose isomerase-containing specimen was added to an aqueous substrate solution containing 0.6 M glucose, 0.01 M $MgCl_2.6H_2O$ and 0.05 M $NaHCO_3$ and having a pH of 8.2. The mixture was maintained at a temperature of 60° C. for one hour to effect isomerization. Then, the amount of fructose produced was determined by a cystein-carbazole sulfuric acid method or a polarimetry method. The activity of the specimen was expressed in terms of the unit of U, which corresponded to the amount of glucose isomerase capable of producing one mg of fructose.

(ii) Activity efficiency (%)

Activity of a glucose isomerase-containing suspension or solution was determined before and after the glucose isomerase immobilizing treatment. The resulting activity values were referred to as "A" and "A'", respectively. Activity of the immobilizing-treated polymeric material was also determined. The resulting activity value was referred to as "B". The activity efficiency was calculated by the equation:

$$\text{Activity efficiency (\%)} = \frac{B}{A - A'} \times 100$$

(iii) Water content

A substrate specimen with which glucose isomerase was to be immobilized was immersed in a bath of water at room temperature for a sufficient period of time to reach saturation. The water clinging to the specimen withdrawn from the water bath was roughly drained off and then absorbed by an absorbent paper. Immediately thereafter, the specimen was weighed. This water immersion and weighing procedure was repeated twice. An average value for the resulting three weights was referred to as "W". The water content was calculated by the equation:

$$\text{Water content} = \frac{W - W_o}{W_o}$$

where $W_o$ is the absolute dry weight of the specimen.

(iv) Adsorption of albumin 100 mg of a substrate specimen with which glucose isomerase was to be immobilized were incorporated in 50 ml of a 0.025 M phosphoric acid buffer solution, having a pH of 7 and containing 150 mg of albumin. The mixture was stirred at room temperature for three hours. After the specimen was withdrawn from the mixture, the amount of albumin remaining unadsorbed in the solution was measured.

EXAMPLES 1 THROUGH 9

40 parts of polypropylene (island ingredient) and 60 parts of a blend (sea ingredient) comprised of 49.5 parts of polystyrene, 1.5 parts of a low molecular weight polystyrene, 7.5 parts of polypropylene and 1.5 parts of a low molecular weight polypropylene were melt-spun at a temperature of 255° C. into composite filaments having an islands-in-a sea type sectional structure (the number of islands=16). The composite filaments were drawn four times their original length in a conventional manner. The filaments had a fineness of 3.7 denier per filament and exhibited a tensile strength of 3.4 g/d and an elongation of 38%.

A blend comprised of 50 parts of polystyrene and 50 parts of polypropylene was melt-spun at a temperature of 250° C. into filaments. The blend filaments so obtained were drawn five times their original length in a conventional manner. The filaments had a fineness of 3.9 denier per filament and exhibited a tensile strength of 2.4 g/d and an elongation of 50%.

The respective islands-in-a sea type composite filaments and blend filaments were β-aminopropionamidomethylated as follows. 1.0 part of the filaments was incorporated in an acrylamidomethylating solution having a composition shown in Table I, below. Then, the filament incorporated solution was maintained at room temperature for six hours. After being extracted with methanol, the filaments were treated in a 20% amine solution in methanol under reflux conditions for two hours. The amines used are shown in Table I, below. The resulting filaments exhibited a tensile strength ranging from 1.0 to 1.5 g/d, and good durability and separation resistance.

hour, to be thereby chloromethylated. Then the chloromethylated filaments were treated in an aqueous 30% trimethylamine solution, to be thereby trimethylam-

TABLE I

| Example No. | Filament | Composition of acrylamidomethylaling solution (parts) | | | | Amine |
|---|---|---|---|---|---|---|
| | | Methylol-acrylamide | sulfuric acid | Nitro-benzene | Paraform-aldehyde | |
| 1 | Islands-in-a-sea type composite filaments | 1.0 | 11.2 | 8.8 | 0 | Dimethylamine |
| 2 | Islands-in-a-sea type composite filaments | 1.0 | 12.4 | 7.6 | 0 | Dimethylamine |
| 3 | Islands-in-a-sea type composite filaments | 1.0 | 12.4 | 7.6 | 0 | N,N-dimethylamino-propylamine |
| 4 | Islands-in-a-sea type composite filaments | 1.0 | 12.4 | 7.6 | 0 | N,N-diethyl-N'-methylethylene diamine |
| 5 | Islands-in-a-sea type composite filaments | 1.0 | 13.8 | 6.2 | 0 | Dimethylamine |
| 6 | Islands-in-a-sea type composite filaments | 1.0 | 10 | 10 | 0.010 | Dimethylamine |
| 7 | Islands-in-a-sea type composite filaments | 1.0 | 10 | 10 | 0.035 | Dimethylamine |
| 8 | Islands-in-a-sea type composite filaments | 1.0 | 10 | 10 | 0.050 | Dimethylamine |
| 9 | Blend filaments | 1.0 | 10 | 10 | 0 | Dimethylamine |

For comparison purposes, islands-in-a-sea type filaments similar to those used in EXAMPLE 8 were acrylamidomethylated in a manner similar to that in EXAMPLE 8. The acrylamidomethylated filaments were treated in concentrated hydrochloric acid, under reflux conditions, for 20 hours, to be thereby hydrolyzed. Then, the hydrolyzed filaments were treated with a formic acid-formalin mixture, to be thereby dimethylaminomethylated.

Furthermore, islands-in-a-sea type composite filaments similar to those used in Examples 1 through 8 were treated in a solution comprised of 5 parts of paraformaldehyde, 25 parts of acetic acid and 70 parts of concentrated sulfuric acid, at a temperature of 80° C., for two hours, thereby forming crosslinks therein. The crosslinked filaments were treated in a solution comprised of 85 parts of chloromethyl ether and 15 parts of stannic chloride, at a temperature of 30° C., for one hour, to be thereby chloromethylated. Then the chloromethylated filaments were treated in an aqueous 30% trimethylamine solution, to be thereby trimethylammoniummethylated.

Glucose isomerase was immobilized with the respective β-aminopropionamidomethylated, dimethylaminomethylated and trimethylammoniummethylated filaments as follows. Glucose isomerase was extracted from "Glucose Isomerase Nagase" (Streptomyces phaeochromogenus, supplied by Nagase Sangyo K.K.). The extract solution was centrifugated to obtain a glucose isomerase extract exhibiting an activity of 3,000 U/20 ml and having a pH of 8. 100 mg of the filaments were incorporated in 20 ml of the glucose isomerase extract, and the obtained mixture was stirred at room temperature for six hours, whereby glucose isomerase was immobilized with the filaments. The filaments used for the isomerase immobilization and the isomerase immobilized filaments had the characteristics shown in Table II, below.

TABLE II

| Example No. | Exchange group | Amount of functional group (meq/g) | Form of functional group *1 | Water content | Albumin adsorption*[3] (mg/g filament) | Activity of isomerase immobilized filaments (U/100 mg) |
|---|---|---|---|---|---|---|
| 1 | β-aminopropion-amidemethyl group | 2.7 | Free | 2.8 | — | 2600 |
| 2 | β-aminopropion-amidemethyl group | 2.6 | " | 1.3 | 200 | 1360 |
| 3 | β-aminopropion-amidemethyl group | 2.0 | " | 1.8 | — | 680 |
| 4 | β-aminopropion-amidemethyl group | 2.0 | " | 2.1 | — | 1330 |
| 5 | β-aminopropion-amidemethyl group | 1.8 | " | 1.0 | — | 850 |
| 6 | β-aminopropion- | 2.9 | " | 2.1 | 570 | 2370 |

TABLE II-continued

| Example No. | Exchange group | Amount of functional group (meq/g) | Form of functional group *1 | Water content | Albumin adsorption*3 (mg/g filament) | Activity of isomerase immobilized filaments (U/100 mg) |
|---|---|---|---|---|---|---|
| | amidemethyl group | | | | | |
| 7 | β-aminopropion- amidemethyl group | 3.0 | " | 1.7 | — | 1410 |
| 8 | β-aminopropion- amidemethyl group | 3.1 | " | 1.5 | 450 | 830 |
| 9 | β-aminopropion- amidemethyl group | 2.9 | " | 1.3 | 130 | 640 |
| *2 Com. 1 | Dimethylamino- methyl group | 3.5 | Free | 1.5 | 600 | 100 |
| Com. 2 | | 3.1 | Cl | 5.1 | 600 | 250 |
| Com. 3 | Trimethylammonium- methyl group | 2.7 | Cl | 2.5 | — | 500 |

*1 "Free" refers to a free form functional group which was formed by treating the filaments in an aqueous 1N sodium hydroxide solution and, then, washing the treated filaments with deionized water. "Cl" refers to a chloride form functional group which was formed by treating the filaments in an aqueous 1N hydrochloric acid solution and, then, wasing the treated filaments with deionized water.
*2 "Com" refers to Comparative Example.
*3 The filaments used for the isomerase immobilization exhibited a tendency of adsorbing invertase and catalase, which was similar to their tendency of adsorbing albumin.

The activity efficiency of the isomerase immobilized filaments of the invention was high, i.e., in the range of from about 80 to 90%.

The following will be seen from Table II. First, the filaments used in the invention have a capacity of immobilizing a large amount of glucose isomerase and, thus, the isomerase immobilized filaments exhibit an enhanced activity per unit weight of the filaments. Secondly, although the filaments used in the invention have a low water content, they exhibit an enhanced activity. This is particularly true where the filaments have little crosslinked structure (Examples No. 1 through 5). Furthermore, in the case where the filaments possess the same functional groups and the same crosslinked structure, the larger the amount of the functional groups, the higher the activity of the isomerase immobilized filaments. In the case where the filaments possess the same functional groups and the same amounts of the functional groups, the lower the degree of crosslinking, the higher the activity of the isomerase immobilized filaments. Also, an organic amine containing a secondary amino group results in the isomerase immobilized filaments exhibiting a higher activity than that of the filaments prepared by using an organic amine containing a primary amino group.

EXAMPLE 10

Islands-in-a-sea type composite filaments similar to those used in Examples 1 through 8 were knitted into a tubular fabric. The tubular knitted fabric was β-aminopropionamidomethylated in a manner similar to that mentioned in Example 2. The resultant fabric had the following characteristics. The amount of the functional group was 2.8 meq/g. The water content (in the free form) was 1.9. The albumin adsorption was 240 mg/g.

A glucose isomerase extract exhibiting an activity of 3,000 U/20 ml was prepared in a manner similar to that mentioned in Examples 1 through 9. The pH of the isomerase extract was adjusted to a value shown in Table III, below, by adding thereto an aqueous 1 N sodium hydroxide solution or an aqueous 1 N hydrochloric acid solution. 100 mg of the above-mentioned knitted fabric having the functional groups in a free form were incorporated in 20 ml of the isomerase extract and the obtained mixture was stirred at room temperature, for six hours, whereby glucose isomerase was immobilized. The resultant fabric had the characteristics shown in Table III, below.

TABLE III

| pH of isomerase extract | Activity of Isomerase immobilized fabric (U/100 mg) | Activity efficiency (%) |
|---|---|---|
| 7 | 710 | 80 |
| 8 | 850 | 81 |
| 9 | 1010 | 80 |
| 10 | 1290 | 77 |
| 11 | 500 | 81 |

As will be seen from Table III, a glucose isomerase extract having a pH of below 10 results in an isomerase immobilized fabric exhibiting a high activity.

EXAMPLE 11

100 mg of a knitted fabric having the functional groups in a free form, which fabric was similar to that mentioned in Example 10, were incorporated in 10 ml of a glucose isomerase extract having an activity of 1,500 U and a pH of 8, which extract was similar to that used in Examples 1 through 9. The mixture was stirred at room temperature, for six hours, whereby glucose isomerase was immobilized. The isomerase immobilized fabric exhibited an activity of 935 U/100 mg. The activity efficiency was 81%. Thereafter, the isomerase immobilized fabric was treated in 10 ml of an aqueous 0.1% glutaraldehyde solution having a pH of 8, at room temperature, for 30 minutes. The resultant fabric exhibited an activity of 900 U/100 mg. The activity efficiency was 78%.

The glutaraldehyde treated fabric was repeatedly used for glucose isomerization. When the fabric was used ten times, it retained 90% of its initial activity. Similarly, the isomerase immobilized glutaraldehyde-untreated fabric was repeatedly used for glucose isomerization. When the fabric was used ten times, it retained 85% of its initial activity.

For comparison purposes, glucose isomerase was immobilized with a commercially available ion exchange resin, Amberlite IRA-904, having trimethylammoniummethyl groups in a chloride form, in a manner similar to that mentioned above. The isomerase immobilized resin exhibited an activity of 450 U/100 mg. The activity efficiency was 75%. This resin retained 65% of its initial activity after ten repeated isomerizations. Similarly, the isomerase immobilized filaments obtained in Comparative Example 3 were repeatedly used for glucose isomerization. The filaments also retained 65% of their initial activity after ten repeated isomerizations.

The above results show that the enzymatically active product of the invention is stable in a substrate solution and, hence, exhibits a good retention of activity. Particularly, the product treated with a multi-functional proteinaceous crosslinking agent, i.e., glutaraldehyde, exhibits an excellent retention of activity.

EXAMPLE 12

100 mg of a knitted fabric having the functional groups in a free form, similar to that mentioned in Example 10, were incorporated in 10 ml of a glucose isomerase extract having an activity of 1,500 U and a pH of 8, similar to that used in Examples 1 through 9. The mixture was stirred at room temperature, for six hours, whereby glucose isomerase was immobilized. The isomerase immobilized fabric exhibited an activity of 935 U/100 mg. The activity efficiency was 81%.

The isomerase immobilized fabric was treated in a substrate solution at a temperature of 90° C., for 10 minutes, whereby the isomerase was deactivated. Then, the fabric was treated in an aqueous 1 M sodium chloride solution, while being stirred, at room temperature, for one hour. Then, the fabric was treated in an aqueous 1 N sodium hydroxide solution, whereby the functional groups were converted to a free form. Thereafter, the fabric was again treated with a glucose isomerase extract in a manner similar to that mentioned above, whereby the isomerase was immobilized. The isomerase immobilized fabric exhibited an activity of 920 U/100 mg. The activity efficiency was 80%.

The above results show that, when the enzymatic activity of the product of the invention is reduced, the product can be regenerated by removing the deactivated enzyme therefrom and then immobilizing the isomerase with the product.

EXAMPLE 13

1 g of a knitted fabric having the functional groups in a free form, similar to that mentioned in Example 10, was incorporated in 75 ml of a glucose isomerase extract suspension containing ruptured cell pieces and exhibiting an activity of 15,000 U. The mixture was stirred at room temperature, for six hours, whereby glucose isomerase was immobilized. The separation of the isomerase immobilized fabric from the ruptured cell-containing suspension could be easily carried out. Thereafter, the isomerase immobilized fabric was treated in 100 ml of an aqueous 0.1% glutaraldehyde solution having a pH of 8, at room temperature, for 30 minutes. The resultant fabric exhibited an activity of 12,500 U. The activity efficiency was 84%. Even when the fabric was treated in an aqueous 1 M sodium chloride solution having a pH of 8, its enzymatic activity was reduced only to a negligible extent.

EXAMPLE 14

A felt was manufactured from islands-in-a sea type composite filaments, which were prepared in a manner similar to that mentioned in Examples 1 through 8, but at a drawing ratio of 3.5 in place of 4.0. The felt was β-aminopropionamidomethylated in a manner similar to that employed in Example 2. The resultant fabric contained 2.8 meq of the β-aminopropionamidomethyl group per g of the fabric and exhibited a water content of 1.9 in a free form of the functional group. Then, the felt was cut into a circular shape. 1.3 g of the circular felt were packed in a column, 1.6 cm in diameter, equipped with a heater. 200 ml of a glucose isomerase extract having an activity of 30,000 U and a pH of 8 were repeatedly passed through the felt-packed column at a temperature of 50° C., for six hours, whereby glucose isomerase was immobilized. The glucose isomerase extract used exhibited an activity of 960 U after the immobilization treatment. Then, an aqueous substrate solution containing 3 M glucose and 0.005 M magnesium sulfate and having a pH of 8 was passed through the column to isomerize glucose. The percentage isomerization was 40% and 45% at flow rates of 75 ml/hr and 55 ml/hr, respectively.

For comparison purposes, 4.5 g of a commercially available ion exchange resin, Amberlite IRA-904, of an $SO_4-$ form were incorporated in 200 ml of a glucose isomerase extract having an activity of 30,000 U and a pH of 8. The mixture was stirred at a temperature of 50° C., for six hours, whereby glucose isomerase was immobilized. The glucose isomerase extract used exhibited an activity of 7,800 U after the immobilization treatment. The isomerase immobilized resin were packed in a column 1.6 cm in diameter equipped with a heater. An aqueous substrate solution similar to that mentioned above was passed through the ion exchange resin packed column at a temperature of 60° C. The percentage isomerization was 40% and 45% at flow rates of 48 ml/hr and 35 ml/hr, respectively.

Furthermore, 10 g of Sweetzyme (trade name for immobilized glucose isomerase supplied by Novo Industri A/S, Denmark) were packed in a column, 1.6 cm in diameter, equipped with a heater. A substrate solution similar to that mentioned above was passed through the column at a temperature of 60° C. The percentage isomerization was 40% and 45% at flow rates of 53 ml/hr and 37 ml/hr, respectively.

The above mentioned results show that the enzymatically active product of the invention exhibits a high activity per unit weight of the product and, consequently, the isomerization of glucose can be effected with a high productivity by passing a substrate solution at an enhanced rate through the active product-packed column.

EXAMPLE 15

100 g of a Y-type zeolite (Y-K, its metal ion was a potassium ion) having a particle size of from 20 to 40 meshes were packed in a column having an inner diameter of 15 mm. The packed zeolite had a height of 92 cm. The isomerized glucose solution obtained in Example 14 and containing 0.55 g of glucose and 0.45 of fructose was continuously supplied into the top of the zeolite packed column at room temperature and at a flow rate of 33 ml/hr, whereby the solution was developed in the column. The effluent withdrawn from the column bottom was sampled at intervals, and it was found that glucose was initially withdrawn and, then, fructose was withdrawn. Analysis of 35 ml of the effluent fractions ranging from 125 ml to 160 ml in total volume of effluent showed that the effluent fractions contained no fructose.

EXAMPLE 16

An isomerized glucose solution obtained by the procedure mentioned in Example 14, and containing 0.6 g of glucose and 0.4 g of fructose, was subjected to adsorption chromatography in a manner similar to that mentioned in Example 15. Analysis of the effluent showed that glucose was initially withdrawn and, then, fructose was withdrawn. The fructose-containing fractions were separated, concentrated and, then, crystallized in a conventional manner, whereby a fructose crystal could be obtained.

What we claim is:

1. A process for isomerizing to produce fructose from glucose, comprising bringing a glucose-containing solution into contact with an enzymatically active product comprising an organic polymeric material comprised of at least 50% by weight, based on the weight of the organic polymeric material, of a monovinyl aromatic compound in polymerized form, said polymerized monovinyl aromatic compound having a β-aminopropionamidomethyl group as a side chain represented by the formula I:

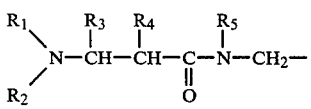   I wherein $R_1$ is selected from hydrogen, an alkyl group having 1 to 6 carbon atoms and a hydroxyalkyl group having 2 to 6 carbon atoms, $R_2$ is selected from an alkyl group having 1 to 6 carbon atoms, a hydroxyalkyl group having 2 to 6 carbon atoms,

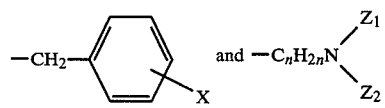

(where X, $Z_1$ and $Z_2$ are selected from hydrogen and an alkyl group having 1 to 6 carbon atoms, and n is an integer of from 2 to 6), or $R_1$ and $R_2$ form together with the nitrogen atom, to which $R_1$ and $R_2$ are bonded, a heterocyclic structure represented by the formula:

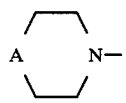

where A is —$CH_2$—, —O— or —$NR_6$-(wherein $R_6$ is H or an alkyl group having 1 to 6 carbons), and $R_3$, $R_4$ and $R_5$ may be the same as or different from each other and are selected from hydrogen and a methyl group, said organic polymeric material having glucose isomerase immobilized with said side chain of the organic polymeric material, whereby at least a part of the glucose is isomerized into fructose.

2. The process according to claim 1, wherein the content of the β-aminopropionamidomethyl group of the formula I is from about 0.5 to 5.0 meq/g of the organic polymeric material.

3. The process according to claim 1, wherein the content of the β-aminopropionamidomethyl group of the formula I is from about 2.0 to 5.0 meq/g of the organic polymeric material.

4. The process according to claim 1, wherein the amount of the immobilized glucose isomerase corresponds to the activity of from 2,000 to 50,000 U per g of the enzymatically active product.

5. The process according to claim 1, wherein the monovinyl aromatic compound is at least one compound selected from the group consisting of styrene, α-methylstyrene, vinyltoluene, vinylxylene and chlorostyrene.

6. The process according to claim 1 wherein the enzymatically active product is in the form of a fiber, a particulate or a film.

7. The process according to claim 6, wherein said product is a fiber, and wherein said fiber comprises, in addition to said organic polymeric material predominantly comprised of the polymerized monovinyl aromatic compound having the β-aminopropionamidomethyl group, a fiber-forming organic polymeric material.

8. The process according to claim 6, wherein said product is a fiber, and wherein said fiber is a core-sheath type or islands-in-a sea type composite fiber, the core or island ingredient being comprised of said fiber-forming organic polymeric material and the sheath or sea ingredient being predominantly comprised of said organic polymeric material predominantly comprised of a polymerized monovinyl aromatic compound having the β-aminopropionamidomethyl group.

9. The process according to claim 6, wherein said product is a fiber, and wherein said fiber is comprised of a mixture of said fiber-forming organic polymeric material and said organic polymeric material predominantly comprised of the polymerized monovinyl aromatic compound having the β-aminopropionamidomethyl group.

10. The process according to claim 7, 8 or 9, wherein said fiber is in the form of non-woven fabric, paper, woven fabric or knitted fabric.

11. The process according to claim 7, 8 or 9, wherein, said fiber forming organic polymeric material is at least one polymer selected from the group consisting of polyolefins, polyamides, polyesters and their copolymers.

12. The process according to claim 1, 7, 8 or 9, wherein the glucose isomerase is cross-linked with a crosslinking agent capable of crosslinking a protein.

13. The process according to claim 12, wherein the crosslinking agent is at least one compound selected from the group consisting of glutaraldehyde, dialdehyde starch, tolylene diisocyanate and hexamethylene diisocyanate.

* * * * *